(12) United States Patent
Lee

(10) Patent No.: US 9,721,817 B2
(45) Date of Patent: Aug. 1, 2017

(54) APPARATUS FOR MEASURING IMPURITIES ON WAFER AND METHOD OF MEASURING IMPURITIES ON WAFER

(71) Applicant: LG Siltron Inc., Gyeongbuk (KR)

(72) Inventor: Seung Wook Lee, Gyeongbuk (KR)

(73) Assignee: LG Siltron Inc., Gyeongbuk (KR)

( * ) Notice: Subject to any disclaimer, the term of this patent is extended or adjusted under 35 U.S.C. 154(b) by 0 days.

(21) Appl. No.: 15/258,959

(22) Filed: Sep. 7, 2016

(65) Prior Publication Data
US 2017/0069515 A1    Mar. 9, 2017

Related U.S. Application Data

(62) Division of application No. 13/425,677, filed on Mar. 21, 2012, now Pat. No. 9,484,273.

(30) Foreign Application Priority Data

Mar. 21, 2011    (KR) .................. 10-2011-0024738

(51) Int. Cl.
*H01L 21/67*    (2006.01)
*H01L 21/66*    (2006.01)
(Continued)

(52) U.S. Cl.
CPC ......... *H01L 21/67288* (2013.01); *G01N 1/32* (2013.01); *G01N 1/34* (2013.01);
(Continued)

(58) Field of Classification Search
CPC . H01L 21/6708; H01L 21/67051; G01N 1/32; G01N 1/4044; G01N 35/0099; G01N 2001/383; G01M 35/0099
See application file for complete search history.

(56) References Cited

U.S. PATENT DOCUMENTS

2003/0084926 A1* 5/2003 Watanabe ................ B08B 3/04
                                                                       134/33
2004/0131783 A1* 7/2004 Lee ........................... B08B 7/00
                                                                       427/352
(Continued)

FOREIGN PATENT DOCUMENTS

EP    1973152 A1    9/2008
JP    10-242228    9/1998
(Continued)

OTHER PUBLICATIONS

Chinese Patent Office Action dated Jul. 28, 2015, issued CN Application No. 201280013923, with English translation, 9 pages.
(Continued)

*Primary Examiner* — Marvin Payen
*Assistant Examiner* — Jeremy Joy
(74) *Attorney, Agent, or Firm* — Lewis Roca Rothgerber Christie LLP

(57) ABSTRACT

Provided are an apparatus for measuring impurities on a wafer and a method of measuring impurities on a wafer. The apparatus includes: a wafer aligning device for aligning a wafer; a loading robot for moving and loading the aligned wafer; a rotation stage for rotating the loaded wafer; a scan robot for holding a natural oxide layer etching solution for the wafer and a metallic impurity recovery solution; and a container for receiving a predetermined etching solution and a recovery solution, wherein the scan robot removes an oxide layer on an edge region of the wafer.

6 Claims, 2 Drawing Sheets

(51) Int. Cl.
   *G01N 1/32* (2006.01)
   *G01N 35/00* (2006.01)
   *G01N 1/40* (2006.01)
   *G01N 1/34* (2006.01)
   *H01J 49/00* (2006.01)
   *G01N 1/38* (2006.01)

(52) U.S. Cl.
   CPC ........ *G01N 1/4044* (2013.01); *H01J 49/0036* (2013.01); *H01L 21/67* (2013.01); *H01L 21/6708* (2013.01); *H01L 21/67051* (2013.01); *H01L 22/12* (2013.01); *G01N 35/0099* (2013.01); *G01N 2001/383* (2013.01)

(56) References Cited

U.S. PATENT DOCUMENTS

| | | | |
|---|---|---|---|
| 2004/0140199 A1* | 7/2004 | Mizohata | C25D 5/04 204/212 |
| 2004/0163670 A1* | 8/2004 | Ko | G01N 1/02 134/2 |
| 2009/0249863 A1* | 10/2009 | Kim | H01L 21/67126 73/31.07 |
| 2012/0260750 A1 | 10/2012 | Lee | |

FOREIGN PATENT DOCUMENTS

| | | | | |
|---|---|---|---|---|
| JP | 10242228 A | * | 9/1998 | ....... H01L 21/67051 |
| JP | 2004347543 A | * | 12/2004 | |
| JP | 2010060439 A | | 3/2010 | |
| KR | 1019970008450 | | 2/1997 | |
| KR | 1020020074757 A | | 10/2002 | |
| KR | 20040001918 A | * | 1/2004 | |
| KR | 1020040001918 A | | 1/2004 | |
| KR | 1020040055934 A | | 6/2004 | |

OTHER PUBLICATIONS

International Search Report dated Oct. 23, 2012, issued in International Application No. PCT/KR2012/002030, 3 pages.

Japanese Office action (without translation) dated Feb. 16, 2016, issued in JP Application No. 2014-501000, 3 pages.

Korea Patent Office Notice of Allowance, dated Feb. 27, 2013, issued in KR Application No. 10-2011-0024738 (without translation), 4 pages.

Korean Patent Office action dated Aug. 23, 2012, issued in KR Application No. 10-2011-0024738 (without translation), 4 pages.

Supplementary European Search Report dated Sep. 22, 2014, issued in EP Application No. 12759915, 2 pages.

* cited by examiner

APPARATUS FOR MEASURING IMPURITIES ON WAFER AND METHOD OF MEASURING IMPURITIES ON WAFER

CROSS-REFERENCE TO RELATED APPLICATIONS

The present application is a divisional of U.S. patent application Ser. No. 13/425,677 filed on Mar. 21, 2012, which claims the priority benefit of Korean patent application number 10-2011-0024738 filed on Mar. 21, 2011, the entire contents of each of which are incorporated by reference herein.

BACKGROUND

The present disclosure relates to an apparatus for measuring impurities on a wafer and a method of measuring impurities on a wafer.

In addition to achieving high integration and miniaturization of a semiconductor device by using a silicon wafer, reducing impurities on the silicon wafer, which drastically deteriorate the semiconductor device, is an important task. Accordingly, analyzing and managing such impurities, especially, metal impurities, are important to manage the quality of a silicon wafer.

According to a related art, a method of measuring metallic impurities on the edge of a silicon wafer includes mounting a wafer in a chamber and introducing hydrofluoric acid vapor into the chamber to remove an oxide layer on an entire surface of the silicon wafer. Then, there is a method of qualitatively and quantitatively analyzing metallic impurities through an inductively coupled plasma mass spectrometer, after immersing the perimeter of the wafer in a solution mixed with hydrogen fluoride, hydrogen peroxide, and hydrochloric acid, and extracting metallic impurities on the perimeter of the wafer while rotating a stage having the wafer mounted.

However, according to a related art, only the edge portion of a silicon wafer needs to be analyzed, but a portion intruding the front and backside surfaces by about 3 mm in addition to the edge of the silicon wafer is analyzed. Accordingly, it is difficult to accurately analyze only the edge portion of the silicon wafer according to the related art.

Moreover, according to a related art, in order to increase a recovery rate of Cu impurity, a mixed solution of hydrofluoric acid, hydrogen peroxide acid and hydrochloric acid is used. However, when hydrochloric acid is used as a recovery solution, because of a material (28Si35Cl) combined with remaining Si on the silicon surface and Cl in hydrochloric acid after an oxide layer on the silicon surface is decomposed, mass interference with 63Cu occurs. Therefore, in inductively coupled plasma mass spectrometry methods, there may be an error in analyzing Cu impurity, which may measure Cu impurity even when there is no Cu impurity.

Additionally, according to a related art, since an oxide layer on an entire wafer surface is removed in order to analyze metallic impurities on the perimeter of the silicon wafer, particles may be easily adsorbed on the front side surface, so that the wafer may not be used as another measurement sample besides a metallic impurity analysis sample.

SUMMARY

Embodiments provide a wafer impurity measuring apparatus and a wafer impurity measuring method, which are capable of qualitatively and quantitatively measuring impurities by selectively extracting the metallic impurities on the edge of a silicon wafer.

Embodiments also provide a wafer impurity measuring apparatus and a wafer impurity measuring method for optimizing a recovery solution.

In one embodiment, an apparatus for measuring impurities on a wafer includes: a wafer aligning device for aligning a wafer; a loading robot for moving and loading the aligned wafer; a rotation stage for rotating the loaded wafer; a scan robot for holding a natural oxide layer etching solution for the wafer and a metallic impurity recovery solution; and a container for receiving a predetermined etching solution and a recovery solution, wherein the scan robot removes an oxide layer on an edge region of the wafer.

In another embodiment, a method of measuring impurities on a wafer includes: aligning a wafer and then loading the wafer on a rotation stage by a loading robot; removing an oxide layer on the edge region of the wafer; collecting metallic impurities on the surface of the wafer edge region having the oxide layer removed, by using a recovery solution; and analyzing the metallic impurities by using the extracted recovery solution.

BRIEF DESCRIPTION OF THE DRAWINGS

The details of one or more embodiments are set forth in the accompanying drawings and the description below. Other features will be apparent from the description and drawings, and from the claims.

DETAILED DESCRIPTION OF THE EMBODIMENTS

Reference will now be made in detail to the embodiments of the present disclosure, examples of which are illustrated in the accompanying drawings.

In the descriptions of embodiments, it will be understood that when a layer (or film), a region, a pattern, or a structure is referred to as being 'on/above/over/upper' substrate, each layer (or film), a region, a pad, or patterns, it can be directly on substrate each layer (or film), the region, the pad, or the patterns, or intervening layers may also be present. Further, it will be understood that when a layer is referred to as being 'under/below/lower' each layer (film), the region, the pattern, or the structure, it can be directly under another layer (film), another region, another pad, or another patterns, or one or more intervening layers may also be present. Therefore, meaning thereof should be judged according to the spirit of the present disclosure. The size of each component is exaggerated for description and thus does not entirely reflect an actual size.

Figure 1:
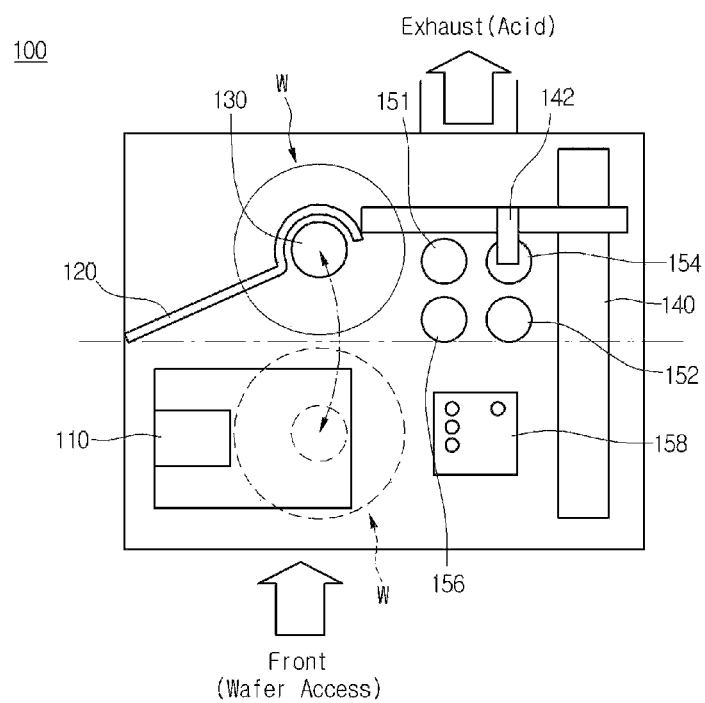
FIG. 1 is a schematic view of an apparatus of measuring impurities on a wafer according to an embodiment.

FIG. 1 is a schematic view of a wafer impurity measuring apparatus 100 according to an embodiment.

The wafer impurity measuring apparatus 100 includes a wafer alignment device 110 for aligning a wafer W, a loading robot 120 for moving the aligned wafer, a rotation stage 130 for rotating the loaded wafer, a scan robot 140 for holding a natural oxide etching solution to the wafer and a metallic impurity recovery solution, and a first container 151 and a second container for receiving a predetermined etching solution and a recovery solution.

The scan robot 140 may move in three-axes (i.e., x-y-z directions).

The scan robot 140 may remove an oxide layer on the wafer edge region.

Additionally, the scan robot 140 may collect metallic impurity on the surface of the wafer edge region having the oxide layer removed, by using the recovery solution.

For example, the scan robot 140 further includes a tube 142 disposed at the bottom end thereof and holding the etching solution and the recovery solution, and the bottom of the tube 142 may have a diagonally-cut shape.

Additionally, the cut region in the bottom end of the tube 142 may be disposed on the lateral side of the wafer edge region.

For example, the recovery solution S (refer to FIG. 3) contacts the wafer edge region in order to collect metallic impurity on the wafer edge region according to an embodiment. At this point, the shape of the tube 142 holding the recovery solution S is important.

According to an embodiment, since the scan robot 140 is disposed above the wafer, if the tube 142 is manufactured being diagonally cut and holds the recovery solution thereon, the recovery solution S contacts substantially only the wafer edge region. If the rotation stage 130 rotates in such a state, metallic impurities on the wafer edge may be collected. The metallic impurities may be quantitatively or qualitatively analyzed through an inductively coupled plasma mass spectrometer by using the collected recovery solution.

The wafer impurity measuring apparatus 100 may include a third container 154 and a fourth container 156 for cleaning the tube 142 of the scan robot 140 and may include a vial tray 158 for containing a sample. The third container 154 may contain a deionized water (DIW) rinse, and the fourth container 156 may contain a chemical rinse, but the present invention is not limited thereto.

According to the wafer impurity measuring apparatus and the wafer impurity measuring method, metallic impurities on the silicon wafer edge region are selectively extracted for a quantitative and qualitative analysis.

Additionally, according to an embodiment, only the natural oxide layer on the wafer edge region is removed, the natural oxide layer on the front side and back side surfaces is not damaged, and also impurities may be minimized, so that the wafer after this measurement may be used as another measurement sample.

Furthermore, according to an embodiment, a recovery rate of impurities may be increased and the mass nesting phenomenon of a mass spectrometer may be resolved by optimizing a recovery solution so that analysis errors may be prevented.

Hereinafter, a method of measuring impurities on a wafer will be described according to an embodiment with reference to FIGS. 1 to 3.

First, the wafer W is aligned, and loaded into on the rotation stage 130 by the loading robot 120.

Figure 2:
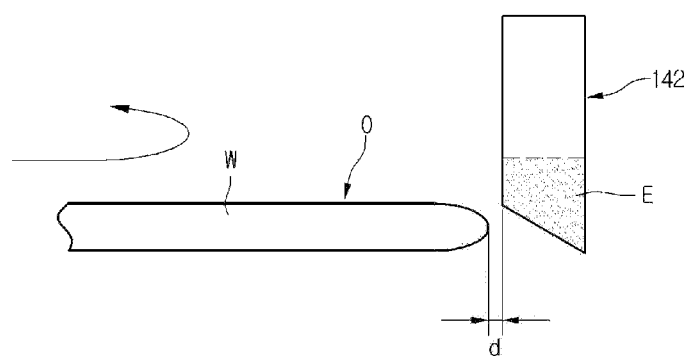
FIG. 2 is a view of when an oxide layer on a wafer edge region being removed according to a method of measuring impurities on a wafer according to an embodiment.

Then, as shown in FIG. 2, the natural oxide layer O on the edge region of the wafer W is removed.

For example, the removing of the oxide layer O on the edge region of the wafer W may include approaching toward the edge region of the wafer W when the scan robot 140 collects and holds an etching solution E, and rotating the rotation stage 130 having the wafer W mounted, not contacting the wafer edge region and being spaced for a predetermined distance d.

The etching solution E may be hydrofluoric acid (HF) but is not limited thereto.

When the natural oxide layer on the wafer edge region is selectively removed using the property that the etching solution E is volatilized at a room temperature, the distance d between the wafer edge region and the tube may be less than about 1 mm, but is not limited thereto. If vaporized etching solution is supplied with the pressure of a predetermined supply device, the distance may be more than and equal to about 1 mm.

An amount of the etching solution E that the scan robot 140 collects and holds is $100\ \mu L \leq V1 \leq 1000\ \mu L$. If an amount of the etching solution E is less than about 100 μL, the oxide layer may not be sufficiently removed, and if more than about 1000 μL, the etching solution E may drop.

According to an embodiment, the scan robot 140 includes a tube 142 disposed at the bottom end thereof and holding an etching solution or a recovery solution, and the bottom of the tube 142 may have a diagonally-cut shape.

Additionally, the cut region in the bottom end of the tube 142 may be disposed on the lateral side of the wafer edge region.

After the natural oxide layer 0 on the wafer edge region is removed, remaining hydrofluoric acid (HF) in the tube 142 of the scan robot 140 may be dumped into a drain, and the tube 142 may be cleaned using DIW in the third container 154.

Figure 3:
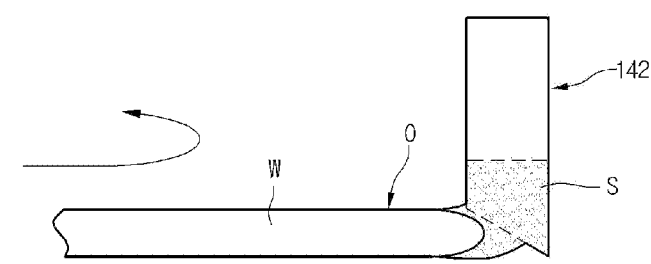
FIG. 3 is a view of when metallic impurities are collected using a recovery solution according to a method of measuring impurities on a wafer according to an embodiment.

Next, as shown in FIG. 3, the metallic impurity on the surface of the wafer edge region having the oxide layer O removed is collected by using the recovery solution S.

For example, the collecting of the metallic impurity on the surface of the wafer edge region by using the recovery solution may include supplying the recovery solution S by using the scan robot 140 and contacting the recovery solution S on the wafer edge region, and extracting the metallic impurity on the wafer edge region by rotating the rotation stage 130.

An amount of the recovery solution S that the scan robot 140 collects and holds is $100\ \mu L \leq V2 \leq 1000\ \mu L$. If an amount V2 of the recovery solution is less than about 100 μL, there is a disadvantage that the number of measurable metallic elements become smaller, and if more than about 1000 μL, a sample volume becomes larger, so that a detectability for a low concentration impurity may be low.

According to an embodiment, the tube 142 disposed at the bottom end of the scan robot 142 holds an etching solution and the bottom of the tube 142 may have a diagonally-cut shape.

For example, the recovery solution S (refer to FIG. 3) contacts the wafer edge region in order to collect metallic impurity on the wafer edge region according to an embodiment. At this point, the shape of the tube 142 holding the recovery solution S is important.

According to an embodiment, since the scan robot 140 is disposed above the wafer, if the tube 142 is manufactured being diagonally cut and holds the recovery solution thereon, the recovery solution S contacts substantially only the wafer edge region.

If the rotation stage 130 rotates in such a state, metallic impurities on the wafer edge may be collected. The metallic impurities may be quantitatively or qualitatively analyzed through an inductively coupled plasma mass spectrometer by using the collected recovery solution.

Moreover, unlike that a mixed solution of hydrofluoric acid, hydrogen peroxide and hydrochloric acid is used as a recovery solution according to a related art, the recovery solution S according to an embodiment may improve a Cu recovery rate by using a mixed solution of hydrofluoric acid and hydrogen peroxide.

In order to improve a recovery rate, the recovery solution may have the chemical composition of X % HF Y % $H_2O_2$ ($0.1 \leq X \leq 5$, $1 \leq Y \leq 28$).

If the composition of HF and $H_2O_2$ is less than the composition range, recovery is poor, and if it is more than the composition range, interference of an Inductively Coupled Plasma/Mass Spectrometer (ICP/MS) may occur and thus accurate measurement may not be obtained.

If the mixed solution of hydrofluoric acid and hydrogen peroxide is used as the recovery solution S, mass interference of 28Si35Cl and 63Cu described above as the disadvantage of the related art may be prevented so that analysis errors may be prevented.

According to the wafer impurity measuring apparatus and the wafer impurity measuring method, metallic impurities on the silicon wafer edge region are selectively extracted for a quantitative and qualitative analysis.

Additionally, according to an embodiment, only the natural oxide layer on the wafer edge region is removed, the natural oxide layer on the front side and back side surfaces is not damaged, and also impurities may be minimized, so that the wafer after this measurement may be used as another measurement sample.

Furthermore, according to an embodiment, a recovery rate of impurities may be increased and the mass nesting phenomenon of a mass spectrometer may be resolved by optimizing a recovery solution so that analysis errors may be prevented.

Figure 4:
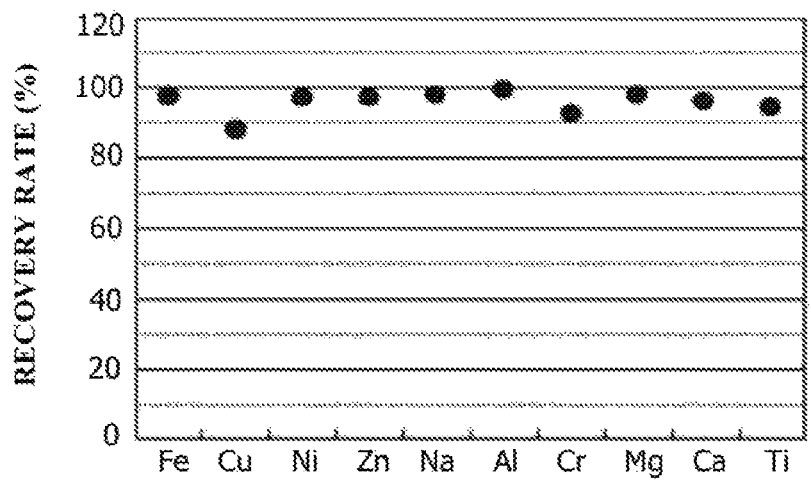
FIG. 4 is a view illustrating a recovery rate of metallic impurities on s wafer edge region when a method of measuring impurities on a wafer according to an embodiment is applied.

FIG. 4 is a view illustrating a recovery rate of metallic impurity measurement on silicon wafer edge region when a method of measuring impurities on a wafer is applied according to an embodiment.

In order to measure a recovery rate of a wafer edge region, if the wafer surface is contaminated through a spin coating method, the wafer edge region in addition to the wafer surface is naturally contaminated during rotation.

Moreover, if the metallic impurities on the front side of the wafer are removed through a VPD/ICP-MS method, the wafer having only the wafer edge region contaminated may be manufactured.

Figure 5:
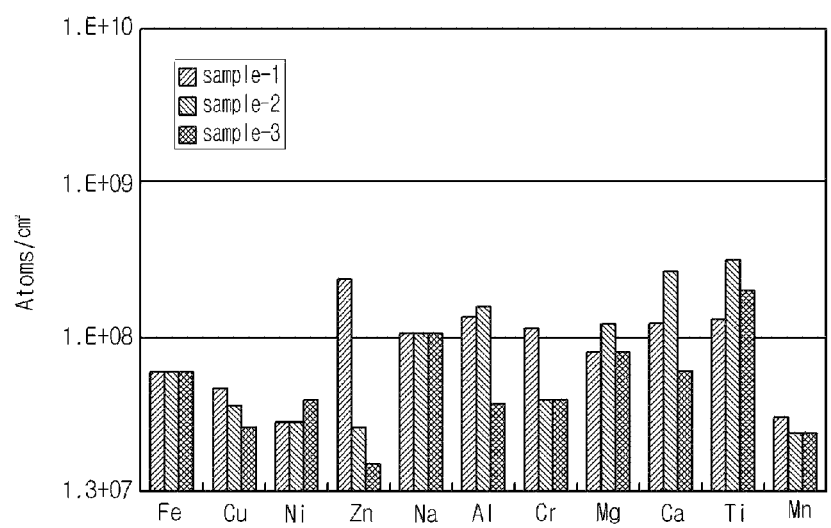
FIG. 5 is a view illustrating measurement results of metallic impurities on a wafer after impurities on a wafer edge region are measured when a method of measuring impurities on a wafer according to an embodiment is applied.

This wafer is repeatedly measured one time, two times, and three times, and a recovery rate is calculated using the equation of [1−(one time measurement concentration/two times measurement concentration)×100]. FIG. 5 shows a result of a recovery rate and the recovery rate of metallic impurity is more than or equal to about 88%. Accordingly, reliability of measurement results of the present invention is excellent.

FIG. 5 is a view illustrating sample results of metallic impurity measurements (Sample-1, Sample-2, Sample-3) on the wafer side after measuring impurities on the wafer edge region when a method of measuring impurities on a wafer according to an embodiment is applied.

According to an embodiment, a natural oxide layer on the front side and back side of the silicon wafer is not damaged, so that the silicon wafer may be used for another measurement after analysis. For example, as shown in FIG. 5, after measuring metallic impurity on the wafer edge region, the metallic impurities on the front side is measured. As a result, the metallic contamination is less than 5E8 atoms/$cm^2$. Therefore, the wafer may be used for Bulk Fe, direct surface oxide defect (DSOD), and thermal treatment evaluations besides the surface metallic impurity evaluation.

According to the wafer impurity measuring apparatus and the wafer impurity measuring method, metallic impurities on the silicon wafer edge region are selectively extracted for a quantitative and qualitative analysis.

Additionally, according to an embodiment, only the natural oxide layer on the wafer edge region is removed, the natural oxide layer on the front side and back side surfaces is not damaged, and also impurities may be minimized, so that the wafer after this measurement may be used as another measurement sample.

Furthermore, according to an embodiment, a recovery rate of impurities may be increased and the mass nesting phenomenon of a mass spectrometer may be resolved by optimizing a recovery solution so that analysis errors may be prevented.

Although embodiments have been described with reference to a number of illustrative embodiments thereof, it should be understood that numerous other modifications and embodiments can be devised by those skilled in the art that will fall within the spirit and scope of the principles of this disclosure.

More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of measuring impurities on a wafer, comprising:
    aligning a wafer and then loading the wafer on a rotation stage by a loading robot;
    removing an oxide layer on an edge region of the wafer by using an etching solution;
    collecting metallic impurities on a surface of the wafer edge region having the oxide layer removed, by using a recovery solution; and
    analyzing the metallic impurities by using the extracted recovery solution,
    wherein the collecting of the metallic impurities on the surface of the wafer edge region having the oxide layer removed comprises:
        holding a recovery solution by a tube disposed at a bottom end of a scan robot;
        lowering the scan robot down to dispose a cut region in the bottom end of the tube on the lateral side of the wafer edge region and contacting the recovery solution, held in the cut region of the tube, to the wafer edge region; and
        extracting the metallic impurities on the wafer edge region while rotating the rotation stage of the wafer.

2. The method according to claim 1, wherein the removing of the oxide layer on the wafer edge region comprises:
    holding the etching solution by the tube of the scan robot;
    lowering the scan robot down to dispose the cut region of the tube on the lateral side of the wafer edge region and contact the etching solution held the cut region of the tube with the wafer edge region; and etching the oxide layer on the wafer edge region while rotating the rotation stage having the wafer mounted.

3. The method according to claim 1, wherein an amount (V1) of the etching solution that the scan robot collects and holds is about 100 μL≤V1≤about 1000 μL.

4. The method according to claim 1, wherein an amount (V2) of the recovery solution that the scan robot collects and holds is about 100 μL≤V2≤about 1000 μL.

5. The method according to claim 1, wherein the recovery solution is a mixed solution of hydrofluoric acid and hydrogen peroxide.

6. The method according to claim 5, wherein the recovery solution has the chemical composition of X % HF Y % $H2O2$ (0.1≤X≤5, 1≤Y≤28).

* * * * *